United States Patent [19]

McLaren

[11] Patent Number: Plant 7,651

[45] Date of Patent: Sep. 17, 1991

[54] NAVEL ORANGE TREE NAMED 'ROHDE SUMMER NAVEL'

[75] Inventor: Peter W. McLaren, Victoria, Australia

[73] Assignee: Harkhill Farm, Victoria, Australia

[21] Appl. No.: 487,890

[22] Filed: Mar. 2, 1990

[51] Int. Cl.[5] ..... A01H 5/00

[52] U.S. Cl. ..... Plt./45

[58] Field of Search ..... Plt./45

[56] References Cited

U.S. PATENT DOCUMENTS

| | | | |
|---|---|---|---|
| P.P. 3,47 | 11/1939 | Workman | Plt. 45 |
| P.P. 6,047 | 12/1987 | Nieuwoudt | Plt. 45 |
| P.P. 6,733 | 4/1989 | Powell et al. | Plt. 45 |
| P.P. 7,342 | 10/1990 | Barnfield | Plt. 45 |

*Primary Examiner*—James R. Feyrer

*Attorney, Agent, or Firm*—Kelly, Bauersfeld & Lowry

[57] ABSTRACT

A new navel orange tree is characterized by relatively late fruit maturity in comparison with other later navel varieties, such as the Lane late navel varieties.

3 Drawing Sheets

1

This invention relates to a new and distinct variety of navel orange tree. The invention is characterized by relative late maturity fruit in comparison with other known late navel varieties, such as the Lane late navel varieties.

The tree is the result of an orange bud sport budded on citrange root stock and discovered in a planting of Marsh Grapefruit located at Harkhill Farm, Red Cliffs, Victoria, Australia. The tree is a mutant or sport of the species citrus sinensis. The approximate geographical location of the tree was latitude 34° 15′ South, longitude 142° 50′ East and at an altitude of about 50 meters above sea level.

The tree was discovered in the course of a deliberate search for new varieties having late maturing fruit, in comparison with other known late navel varieties. In this regard, the closest known navel varieties are Summer Gold late navel, Autumn Gold late navel, Powell late navel, Edwards late navel, Barnfield late navel, Chislett late navel, Toomey summer navel, Lane (Garraway) late navel, and Lane (Christensen) late navel.

Reproductions of the tree were made by propagating buds on Citrange root stock. Trees resulting from such propagation are stable and true to type when compared with the parent tree in all distinguishing characteristics. The asexual reproduction of this tree by budwood has resulted in a navel orange tree with late fruit maturity, in comparison with other late navel varieties, particularly with respect to varieties such as Lane late navel varieties. The fruit reaches a mature state approximately sixty days later than the fruit of Lane late navel varieties, and thereafter remains in good condition on the tree for a period of up to about ninety days. In other respects, the tree and fruit generally conform with the characteristics of other known navel orange trees. Observation of the new tree may be made at Harkhill Farm, Red Cliffs, Victoria, Australia.

The accompanying photographs show the tree and fruit of the present invention. In such photographs:

2

Figure 3:
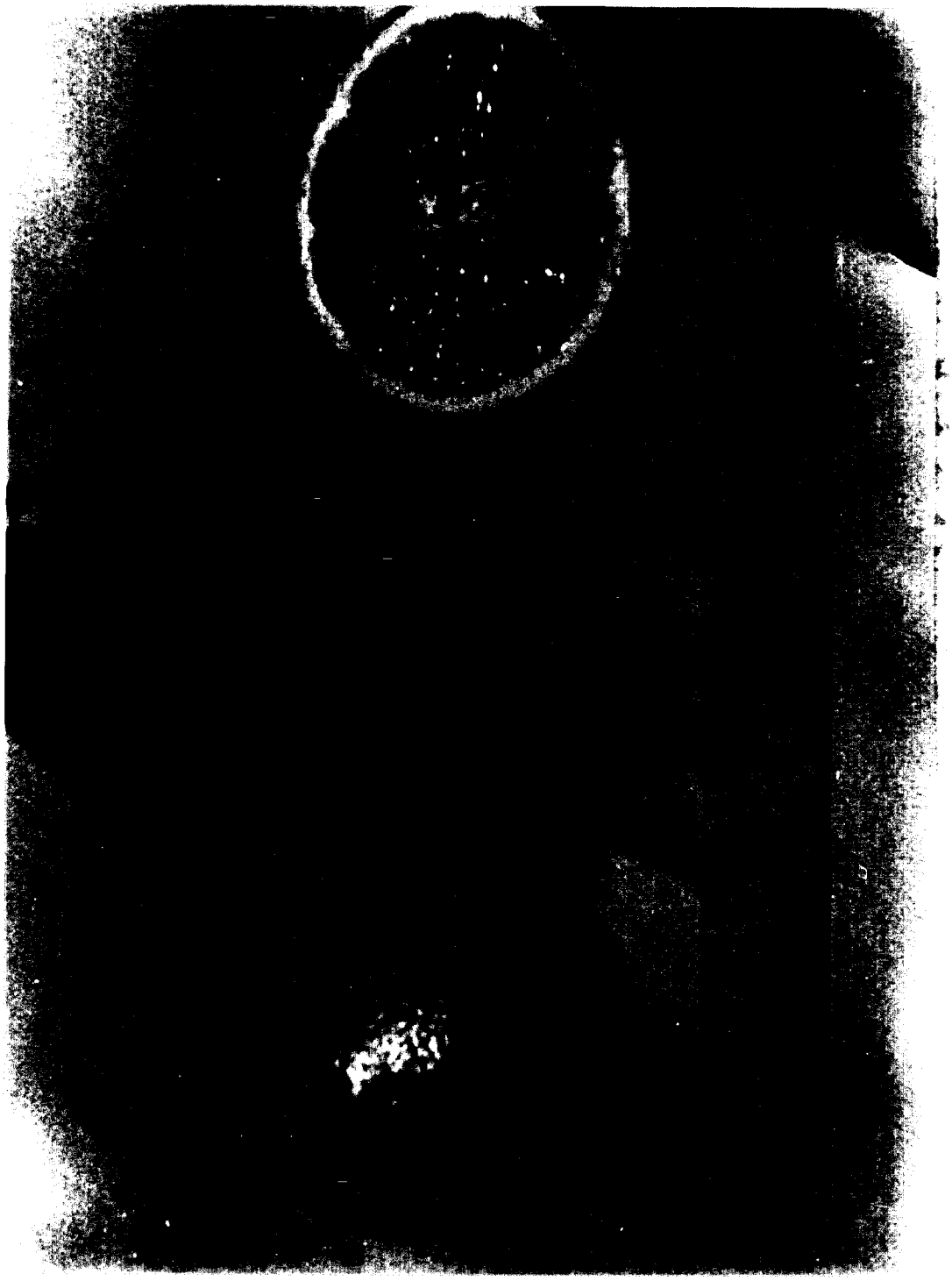
Figure 2:
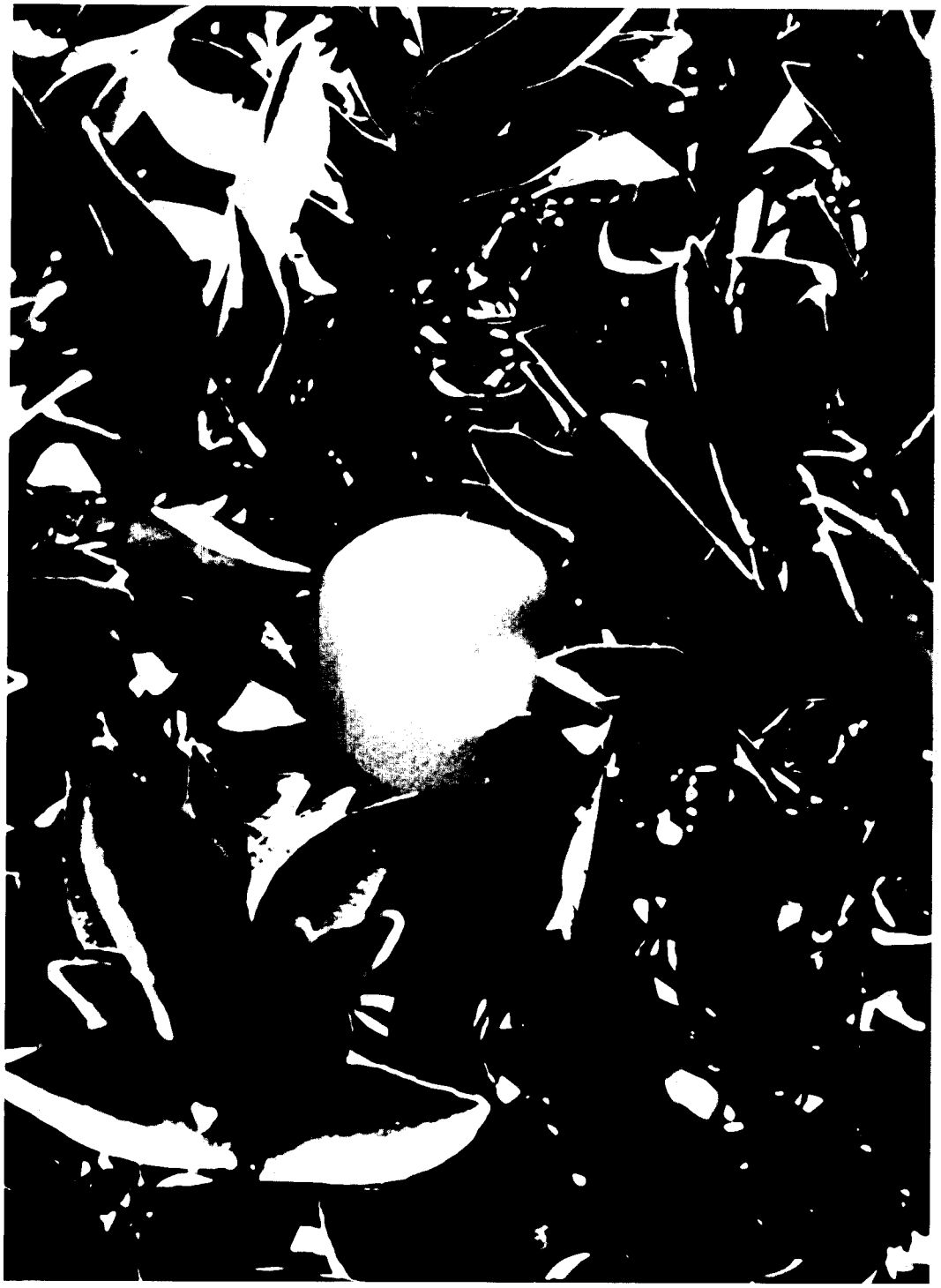
FIG. 2 is an enlarged view illustrating the foliage of the tree of FIG. 1 and depicting fruit thereon.
Figure 1:
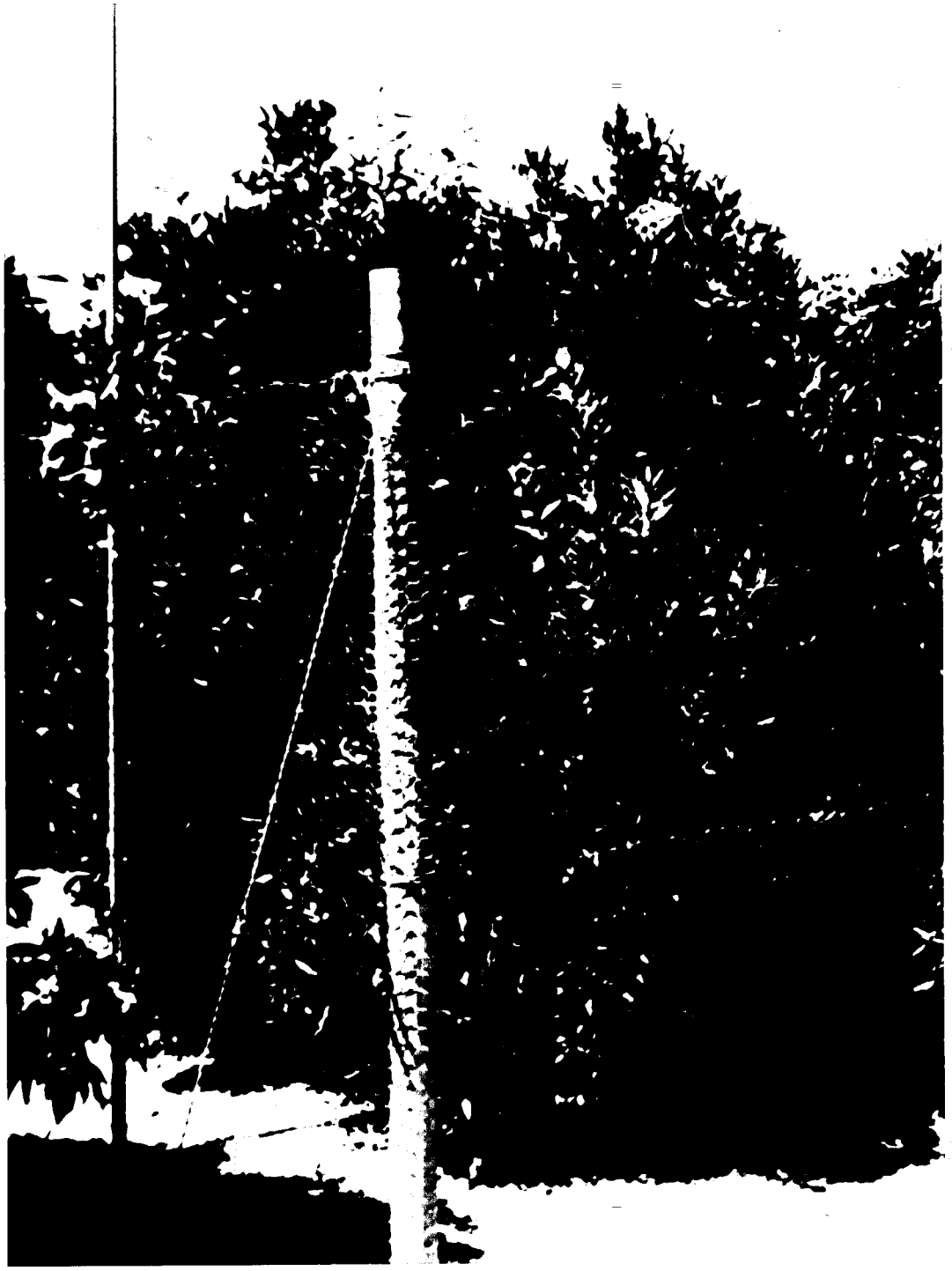
FIG. 1 shows the navel orange tree of the present invention.

FIG. 3 shows an example of foliage cut from the tree, together with fruit therefrom depicted in whole and in half.

The following is an outline description in greater detail of the new and distinct variety of navel orange tree of the present invention:

PLANT

Form: Tree.

Growth: Strong and vigorous growth with spreading foliage, mature height of approximately 3 meters and mature spread of approximately 4–4.5 meters.

Wood: Medium size and height with relatively smooth bark of dark brown color. Limbs of generally rounded shape and irregular array.

*Mature wood.*—R.H.S. (Royal Horticultural Society) Color Chart, green group, card 193C. New wood: R.H.S. color chart, yellow-green group, card 143C. Thorns are present on both new and mature wood.

Foliage: Single leaf in abundant density, having an average size of approximately 100–110 millimeters and a breadth of approximately 50–55 millimeters. Upper surface is glossy smooth and dark green, whereas lower surface is pale green. General shape is variable elliptical, with narrowed base and acute apex. Leaves exhibit moderate thickness. The length of mature leaves is about 58.2 mm, and the corresponding breadth is about 22.2 mm. The leaves have a narrowed base in combination with acute acumination at the apex. Venation is distinct. Marginal oil cells are numerous with a size of about 27.04 sq. cm. Petiole has a winged shape.

Fruit: Good quality commercial grade with average weight approximately 280–340 grams. Fruit shape is globose with depressed and furrowed base, evenly rounded and slightly parted apex, and open protruding navel. With external diameter of about 5.1 mm. Average circumference is about 25–30 centimeters, average length is about 8–9 centimeters and average width is about 8–9 centimeters. Rind color is deep orange with relatively strong aroma, moderately rough or pebbled exterior surface with significant adherence to pulp and late season puffing. Stem is straight and short to medium length with a stout thickness and dark green in color, with relatively even depressed calyx and sepals. Average calyx size is about 6 millimeters.

Rind is relatively free and smoothly pebbled with a thickness of about 9 to 10 millimeters at apex, about 5–6 millimeters at median, and about 4–5 millimeters at base. Rind oil cells are medium sized. Rind color on Minolta color meter a:b ratio=0.22. Approximately sixty percent of samples regreened on 10–50 percent of surface. Most orange color: R.H.S. Color Chart, yellow-orange group, card 23A. Most green color: R.H.S. color chart, yellow-green group, card 145A. Peeling characteristics have not been established scientifically but are generally similar to Lane late navel. Fruit has approximately 9–12 segments of variable shape and easy separation. Fruit color is deep orange. Fruit exhibits relatively fine yet firm texture with light granulation and medium/large vesicles. Fruit is seedless. Flesh color on Minolta color chart meter a:b ratio=0.14; R.H.S. Color Chart, orange group, card 25A. Juice distribution is somewhat deficient at basal with juice proportion at about 55 percent. Juice color on Minolta color meter a:b ratio=0.14; R.H.S. Color Chart, yellow-orange group, card 25A. Juice flavor is sweet and subacid. Pith is hollow.

Fruit maturity peaks up to sixty days later than comparable varieties, such as Lane late navel, and remains in good condition on the tree for up to ninety days following maturity. For example, in northwestern Australia, fruit reaches peak maturity in February, in comparision with Lane late navel which reaches peak maturity in December to early January. The fruit remains in good condition for on-tree storage until April in northwestern Australia, in comparison with Lane late navel which remains in good condition for on-tree storage until March. Fruit productivity for mature tree is about 80–110 kilograms per tree.

Blossom: Blossoms generally similar to Lane late navel, having approximately 25 stamens and a depressed calyx.

*Anther color.*—R.H.S. Color Chart, grey-yellow group, cards 162A and 162B. Blossoms set approximately at the same time as Lane late navel (about October 5 in northwestern Australia) and last for about 10–12 days.

Cultivator name: "Rhode Summer Navel".

The tree and its fruit as described herein may vary in slight detail due to climatic or soil conditions under which the variety is grown.

What is claimed is:

1. A new and distinct variety of navel orange tree substantially as shown and described, characterized particularly as to novelty by a relatively late maturing fruit in comparison with other known late navel varieties.

* * * * *